US010252098B2

(12) United States Patent
Wilke

(10) Patent No.: US 10,252,098 B2
(45) Date of Patent: Apr. 9, 2019

(54) FINE WEIGHT-ADJUSTMENT DEVICE FOR FREE-WEIGHT FITNESS EQUIPMENT

(71) Applicant: Christopher Michael Wilke, Del Mar, CA (US)

(72) Inventor: Christopher Michael Wilke, Del Mar, CA (US)

( * ) Notice: Subject to any disclaimer, the term of this patent is extended or adjusted under 35 U.S.C. 154(b) by 7 days.

(21) Appl. No.: 15/271,737

(22) Filed: Sep. 21, 2016

(65) Prior Publication Data

US 2017/0080275 A1    Mar. 23, 2017

Related U.S. Application Data

(60) Provisional application No. 62/222,675, filed on Sep. 23, 2015.

(51) Int. Cl.
| | |
|---|---|
| *A61B 5/00* | (2006.01) |
| *A61B 5/11* | (2006.01) |
| *A63B 21/00* | (2006.01) |
| *A63B 21/02* | (2006.01) |
| *H04M 1/725* | (2006.01) |

(Continued)

(52) U.S. Cl.
CPC ............ *A63B 21/075* (2013.01); *A61B 5/11* (2013.01); *A61B 5/6895* (2013.01); *A63B 21/00065* (2013.01); *A63B 21/0726* (2013.01); *A61B 2505/09* (2013.01); *A63B 21/023* (2013.01); *A63B 21/072* (2013.01); *A63B 21/0724* (2013.01); *A63B 21/0728* (2013.01); *A63B 2209/08* (2013.01); *A63B 2209/14* (2013.01); *A63B 2220/10* (2013.01); *A63B 2220/30* (2013.01); *A63B 2220/40* (2013.01);

(Continued)

(58) Field of Classification Search
CPC ...................................... A63B 21/072–21/075
See application file for complete search history.

(56) References Cited

U.S. PATENT DOCUMENTS

| 1,703,679 A | * | 2/1929 | Matters | .................... A45D 6/18 |
| | | | | 132/243 |
| 5,749,814 A | * | 5/1998 | Chen | .................. A63B 21/0004 |
| | | | | 473/437 |

(Continued)

OTHER PUBLICATIONS

Form. "Form Collar." http://www.formlifting.com/#homepage. Last accessed on Dec. 8, 2016.

(Continued)

*Primary Examiner* — Jennifer M Deichl
(74) *Attorney, Agent, or Firm* — Arc IP Law, PC; Joseph J. Mayo

(57) ABSTRACT

The disclosure provides a device for fine weight adjustment of a host apparatus. The host apparatus can be a free weight or similar having a bar with a bar diameter. The device can have an annular or disc-shaped body. The annular body can have an inner disc perimeter defining a central aperture having a diameter substantially similar to the bar diameter of the host apparatus. The annular body can also have a slot extending through the annular body from an outer perimeter to the central aperture defining a first disc end and a second disc end separated by a slot width. The annular body can be formed of a material having an elasticity sufficient to allow axial flexibility that returns the annular body to its original shape after being deformed to fit around the bar of the host apparatus.

14 Claims, 7 Drawing Sheets

(51) Int. Cl.
 *A63B 21/072* (2006.01)
 *A63B 21/075* (2006.01)
(52) U.S. Cl.
 CPC ....... *A63B 2220/51* (2013.01); *A63B 2225/50* (2013.01); *H04M 1/7253* (2013.01)

(56) References Cited

U.S. PATENT DOCUMENTS

| | | | | |
|---|---|---|---|---|
| 7,494,451 B1 * | 2/2009 | Ramos | ............... | A63B 21/0728 482/107 |
| 2016/0375295 A1 * | 12/2016 | Brasch | ............... | A63B 21/0728 482/107 |

OTHER PUBLICATIONS

Valle. "Top 10 Power Measurement Tools in Strength and Conditioning." Freelap USA. https://www.freelapusa.com/top-10-power-measurement-tools-in-strength-and-conditioning/. Last accessed on Dec. 8, 2016.

* cited by examiner

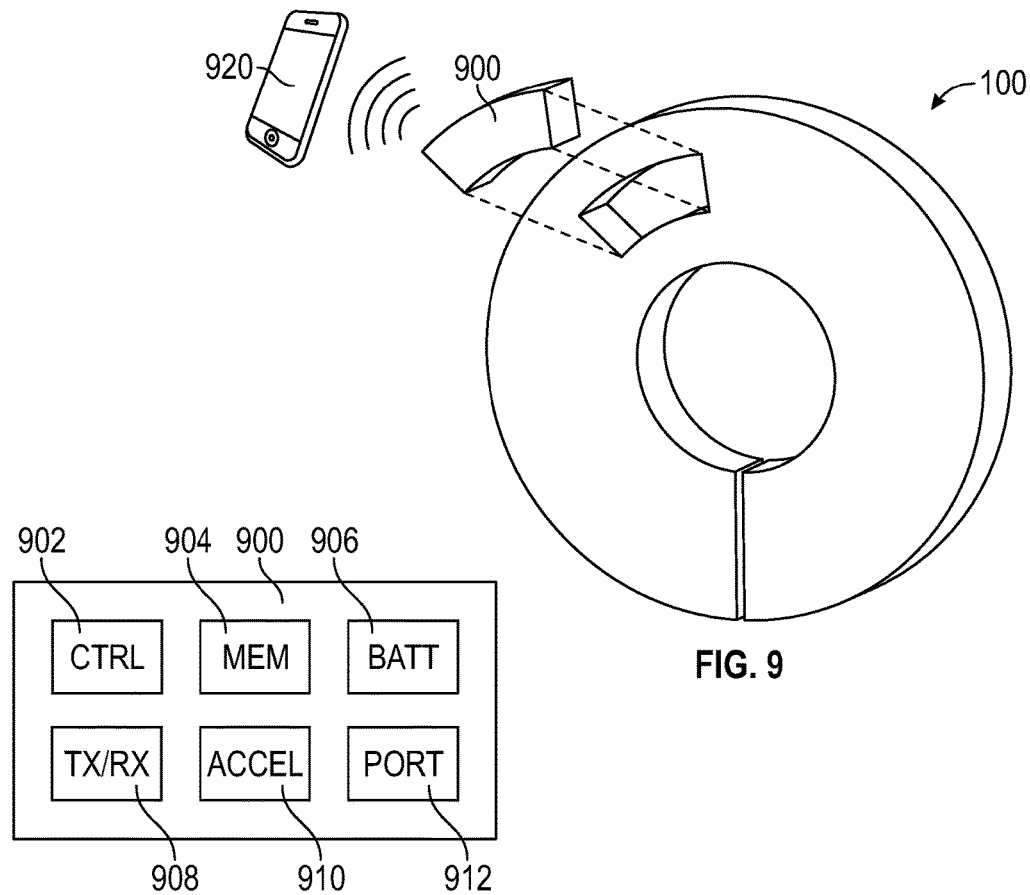
FIG. 9
FIG. 10
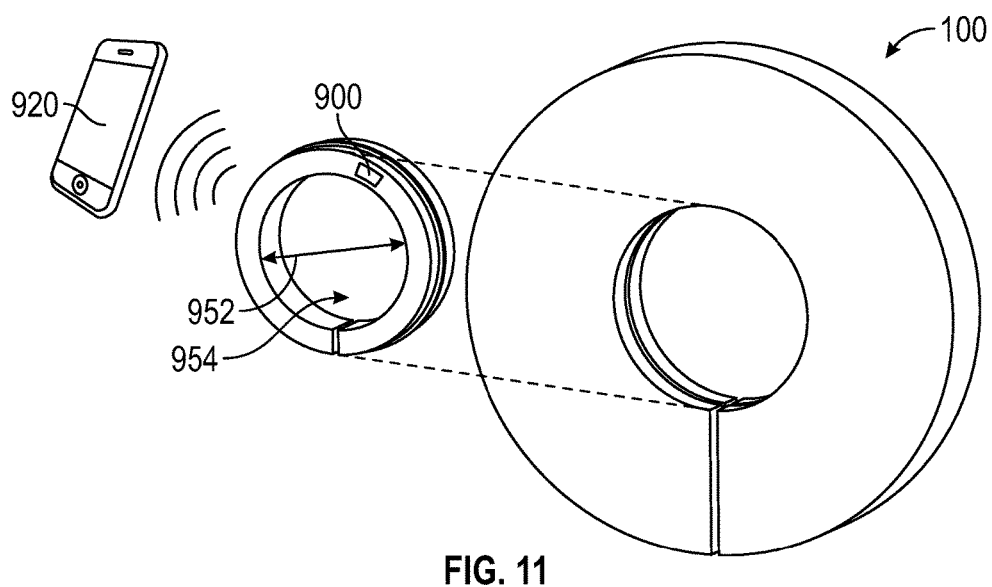
FIG. 11

FINE WEIGHT-ADJUSTMENT DEVICE FOR FREE-WEIGHT FITNESS EQUIPMENT

CROSS REFERENCE TO RELATED APPLICATIONS

This application claims priority to U.S. Provisional Application, 62/222,675, filed Sep. 23, 2015, entitled "FINE WEIGHT ADJUSTMENT," the contents of which are hereby incorporated by reference in their entirety.

BACKGROUND

Technological Field

This disclosure relates to fitness products. More specifically, this disclosure relates to fine weight adjustment for weight lifting devices such as free weights.

Related Art

In the realm of fitness products, dumbbells, barbells, kettle bells, and similar free weights can be produced in fixed sizes with inflexible weight adjustment. In some examples, fixed-weight bar bells or dumbbells may be available in five pound (lb.) or 10 lb. increments or analogous metric denominations (e.g., 5 kilograms (kg)). While the five or ten pound increments provide a certain amount of flexibility in a user's workout, fixed-weight bar bells and dumbbells have no provision for user-adjustable weight denominations. This can limit flexibility in selecting appropriate weights for a given workout routine.

SUMMARY

In general, this disclosure describes systems and methods related to fine weight adjustment device for a host apparatus, particularly for weightlifting or free-weight fitness systems. The systems and devices of this disclosure each have several innovative aspects, no single one of which is solely responsible for the desirable attributes disclosed herein.

One aspect of the disclosure provides a device for fine weight adjustment of a host apparatus having a bar with a bar diameter. The device can have an annular body. The annular body can have an outer disc perimeter. The annular body can also have an inner disc perimeter, the inner disc perimeter defining a central aperture, the central aperture having a diameter substantially similar to the bar diameter of the host apparatus. The annular body can also have a slot extending through the annular body from the outer disc perimeter to inner disc perimeter and defining a first disc end and a second disc end separated by a slot width. The annular body can be formed of a material having an elasticity sufficient to allow axial flexibility that returns the annular body to its original shape after being deformed.

Another aspect of the disclosure provides a device for fine weight adjustment of a host apparatus for use in fitness activities, the host apparatus having a bar with a bar diameter. The device can have an annular body. The annular body can have an outer disc perimeter. The annular body can also have an inner disc perimeter, the inner disc perimeter defining a central aperture, the central aperture having a diameter sufficient to receive the bar diameter of the host apparatus. The annular body can also have a slot extending through the annular body from the outer disc perimeter to inner disc perimeter and defining a first disc end and a second disc end separated by a slot width.

Another aspect of the disclosure provides a device for incremental weight adjustment of a host apparatus for use in fitness activities, the host apparatus having a bar with a bar diameter. The device can have a disc body having a first disc end, a second disc end, and a hollow interior, the disc body forming a portion of an annulus. The device can also have a retractable arm housed within the hollow interior in a clearance fit and extending out the second disc send, the retractable arm having an interior end opposite a rounded end, the rounded end being proximate the first disc end. The device can also have an internal spring mechanism housed within the hollow interior. The internal spring mechanism can have a spring first end in contact with the interior end of the retractable arm, and be operable to apply a force to the retractable arm toward a closed position.

Other features and advantages of the present disclosure should be apparent from the following description which illustrates, by way of example, aspects of the disclosure.

BRIEF DESCRIPTION OF THE FIGURES

The details of embodiments of the present disclosure, both as to their structure and operation, may be gleaned in part by study of the accompanying drawings, in which like reference numerals refer to like parts, and in which:

FIG. 9 is a perspective view of another embodiment of the device of FIG. 1;

FIG. 10 is a functional block diagram of the fitness monitor of FIG. 9;

FIG. 11 is a perspective view of another embodiment of the device of FIG. 9;

DETAILED DESCRIPTION

The detailed description set forth below, in connection with the accompanying drawings, is intended as a description of various embodiments and is not intended to represent the only embodiments in which the disclosure may be practiced. The detailed description includes specific details for the purpose of providing a thorough understanding of the embodiments. In some instances, well-known structures and components are shown in simplified form for brevity of description. In addition, for ease of description and drawing, certain features may not be drawn to scale in all cases.

By way of example, the disclosure includes various embodiments of a fine weight adjustment device. The device can have a stable connection to any weight or weightlifting apparatus (host apparatus) with compatible geometry. The fine weight adjustment device is adapted to be manipulated (e.g., twisted, compressed, etc.) in such a way that opens a slot to a sufficient width allowing the fine weight adjustment device to be attached to the host apparatus.

In strength training and rehabilitation, load progressions of five percent or less are beneficial for safe and effective progress. In some cases a personal or home gym or even the large commercial gyms may only offer free weights or load progressions of five pounds or more. Such environments do not have sufficient storage or space for large numbers of free weights that increase in weight by increments of less than five lbs. Such an arrangement does not allow for an individualized weight progression plan.

Figure 1:
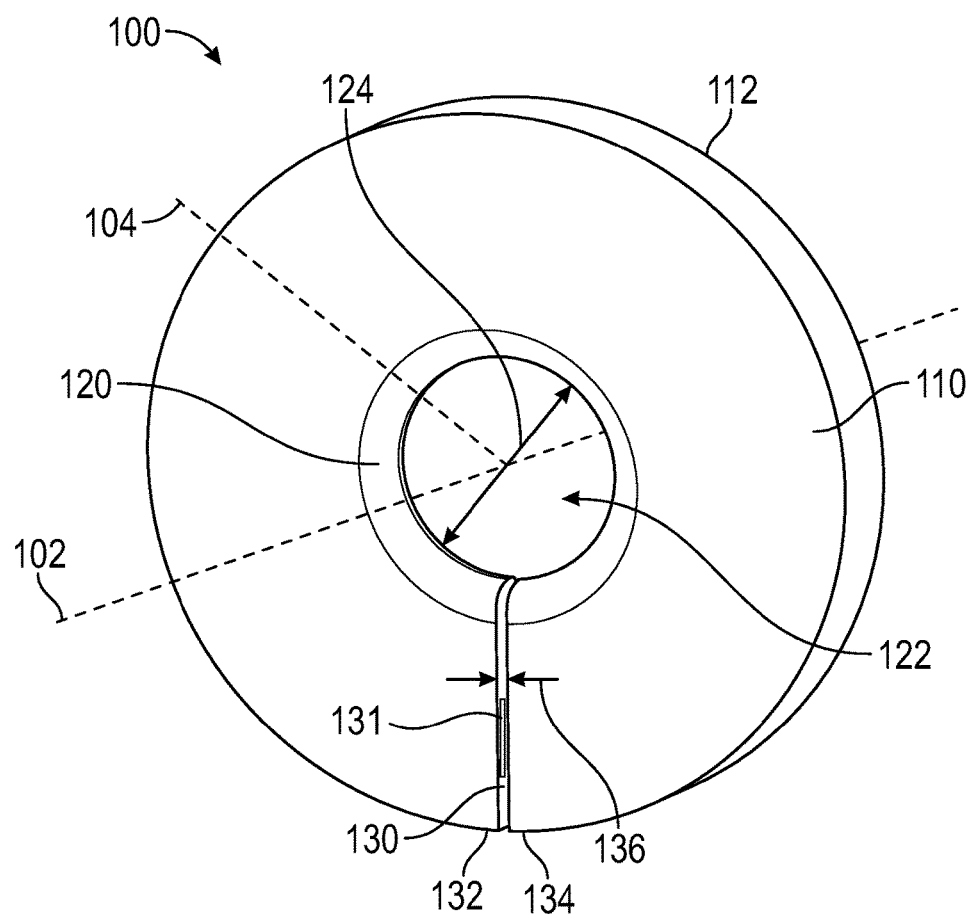
FIG. 1 is a perspective view of an embodiment of a device for fine weight adjustment of a free-weight.

FIG. 1 is a perspective view of an embodiment of a device for fine weight adjustment for a free-weight device. A fine weight adjustment device (device) 100 can be adapted to fit onto a weight bar of a free-weight device (see below) or other weight-lifting apparatuses. The weight-lifting apparatus onto which the device 100 is installed may be referred to herein as a "host apparatus" (see FIG. 5). The various host apparatuses can have a fixed-weight or variable-weight configuration. The device 100 can be annular or disc-shaped, having a disc portion 110 and a ring portion 120. The disc portion 110 can have an outer perimeter 112 and be coupled to the ring portion 120 permanently or temporarily, as described in the connection with the following figures. In some embodiments, the ring portion 120 can be an inner-ring that provides a stable connection to the bar of the host apparatus, such as, for example, any free-weight device including barbells, dumbbells, kettlebells, etc. The disc portion 110 and the ring portion 120 can form an annular body.

The device 100 can have a central axis 102 (shown as a dashed line) extending through the center of the ring portion 120. The central axis 102 is generally orthogonal to the plane of the device 100. Accordingly, as used herein, the "axial direction" may be used to refer to movement along the central axis 102. (See also FIG. 3). The central axis 102 is generally coincident with an axis of a bar or handle of the host apparatus.

The device 100 can also have a radial direction 104 also shown as a dashed line. The radial direction 104 can describe any direction away from the central axis 102, about the circumference of the device 100. The radial direction 104 is orthogonal to the central axis 102.

The disc portion 110 can be an outer disc, annulus, or ring that can provide a specific or desired weight. Together with the ring portion 120, the device 100 can have a desired total weight (or mass) that can be applied to the host apparatus for incremental weight progression. In some embodiments, the device 100 can have a total weight of one-quarter lb., one-half lb., three-quarter lb., one lb., or any denomination therebetween. In some embodiments, the device 100 can have whole pound denominations from 1, 2, 3, 4, or 5 lbs. Accordingly, the use of any pair of devices 100 can result in a specific or desired load (e.g., 4 lbs.+0.75 lb=4.75 lbs.) In some examples the device 100 can be used in pairs for such an incremental weight increase.

In some embodiments the disc portion 110 and the ring portion 120 can be made of the same material and may be a single piece. In other embodiments, the disc portion 110 and the ring portion 120 can be made from different materials and bonded together. The disc portion 110 and the ring portion 120 can be coupled together permanently by the use of an adhesive or temporarily by way of an interference fit, as describe in connection with FIG. 8B, below. In some other embodiments, the device 100 can be formed as a unitary piece.

The disc portion 110 and the ring portion 120 can be formed of a flexible material such as a polymer or composite material. In some examples, certain plastics or polymers can have sufficient flexibility and weight for such a purpose. In some other embodiments, a composite mixture of a light-weight material (e.g., a polymer) can be combined with another heavier material or weight elements such as for example, a metallic material (e.g., a powder or small metallic portions) that can add weight while minimizing the impact on the flexibility of the device 100. In some other embodiments, weight elements (e.g., in any shape, including pellets/powder, arcs, disks, pie-shaped wedges, etc.) may be added to the device 100 during formation of the disc portion 110 and/or the ring portion 120. For example, the disc portion 110 can be formed from a polymer or plastic that is cured from a liquid material. Thus, while in liquid form, various weight elements can be added to the mixture to form the disc portion 110 having a desired total weight and flexibility. The synthetic construction of the device 100 from such a flexible and/or composite material can provide a degree of axial flexibility of device 100. In some embodiments, the ring portion 120 and the disc portion 110 can have different degrees of flexibility. In some embodiments, the ring portion 120 and the disc portion 110 can the same degree of flexibility. This is described in more detail in connection with FIG. 4.

Figure 2:
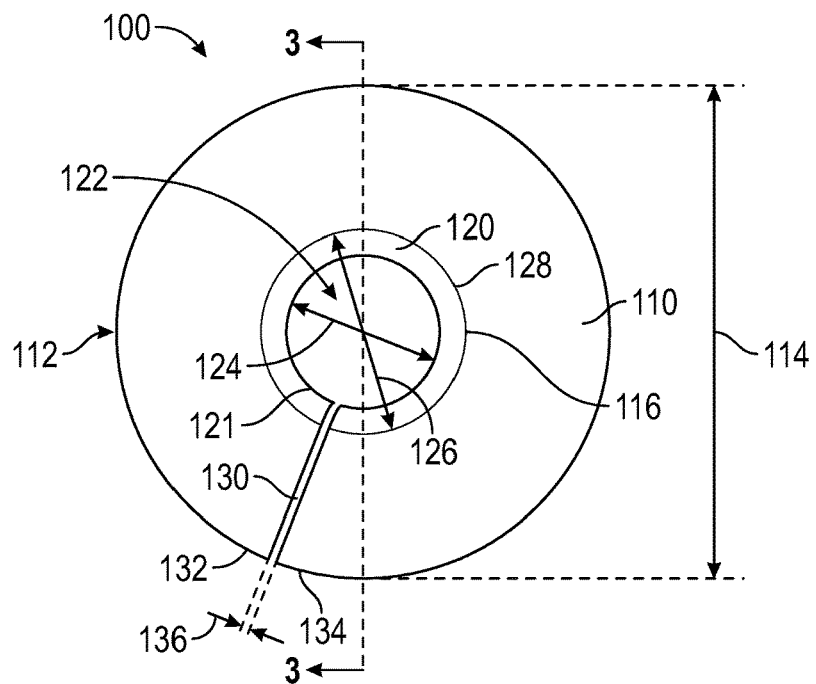
FIG. 2 is a plan view of the device of FIG. 1.

FIG. 2 is a plan view of the device of FIG. 1. The device 100, or more specifically, the disc portion 110 can have a disc outer diameter 114. The disc portion 110 can also have a disc inner perimeter 116 coincident with a ring outer perimeter 128 of the ring portion 120. The ring outer perimeter 128 and the disc inner perimeter 116 can have a substantially similar diameter 126. In embodiments having a separate disc portion 110 and ring portion 120, the diameter 126 can provide an interference fit between the disc portion 110 and the ring portion 120.

Figure 5:
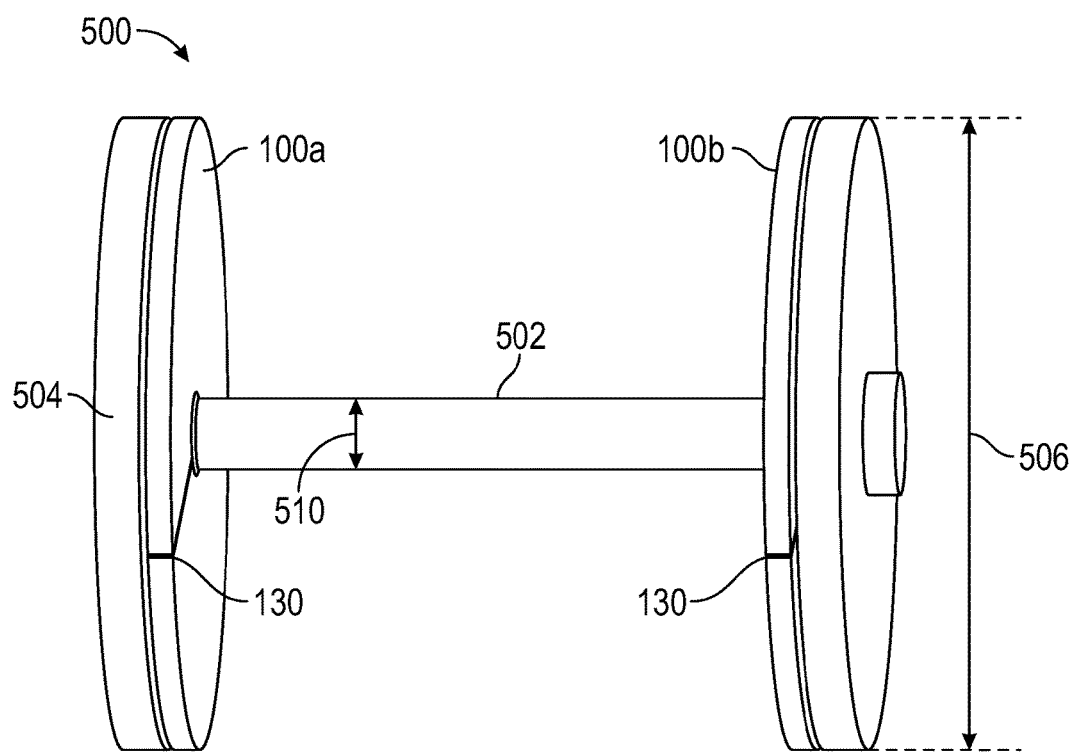
FIG. 5 is a perspective view of the device of FIG. 1 installed on a host apparatus.

The ring portion 120 can have a ring inner perimeter 121 that defines a central aperture 122. The central aperture 122 can have an inner diameter 124. The inner diameter 124 can be similar to a diameter of the host apparatus into which the device 100 is applied. For example, the inner diameter 124 can be slightly larger than a bar of a barbell or dumbbell, or handle of a kettle bell (FIG. 5). In some embodiments, the inner diameter 124 can be approximately one inch to two inches, depending on the application. In some examples a weightlifting bar can be, for example, approximately 1.1 inches in diameter. Accordingly, the inner diameter 124 can be slightly larger. For example, the inner diameter can be 1.15 in., 1.2 in., 1.25 in., or another dimension that provides sufficient clearance and a secure fit of the device 100 to the host apparatus.

The device 100 can have a radial slot 130. The radial slot 130 can extend from the central aperture 122 at the ring inner perimeter 121, outward in a generally radial direction through the disc portion 110 to the disc outer perimeter 112. Thus the radial slot 130 penetrates both the disc portion 110 and the ring portion 120. One of ordinary skill will also appreciate that the radial slot 130 is not limited to a direction orthogonal to the central axis 102. The radial slot 130 can have another angles extending from the central aperture 122 through the ring portion 120 and the disc portion 110 to a point on the outer perimeter 112.

The radial slot 130 can define a first end 132 and a second end 134 of the device 100. The first end 132 and the second end 134 can be separated by a slot width 136. The radial slot 130 and the (axial) flexibility of the disc portion 110 and the ring portion 120 can allow first end 132 to be deflected from the second end 134 in an axial direction. The device 100 can then be used as a fine weight adjustment to be fit onto any host apparatus with compatible geometry. The slot width 136 can be in the range from 1.0 mm or 2.0 mm. The slot width 136 can also be 0.05, 0.1, or 0.2 inches, or larger as required.

In some embodiments, the first end 132 and the second end 134 can each be magnetically attracted to each other. The first end 132 and the second end 134 can be fitted or formed with a magnetic material 131 (FIG. 1) (e.g., a permanent magnet). The magnetic materials can be magnetically attracted to one another, securing the device 100 in place. Only the magnetic material 131 is shown on the first end 132 in the embodiment of FIG. 1 however it should be appreciated that the second end 134 can have a complementary magnetic material 131.

In some embodiments, the device 100 can have a specific weight. Further, any number of adjustment plates 100 can be coupled to a host apparatus to achieve the desired total weight. For example, the device 100 can have a total weight of one-quarter lb., one-half lb., three-quarter lb., one lb., two lbs., three lbs., four lbs., or five lbs. In some other embodiments, any denomination therebetween can also be implemented to provide incremental load progression on the host apparatus.

Figure 3:
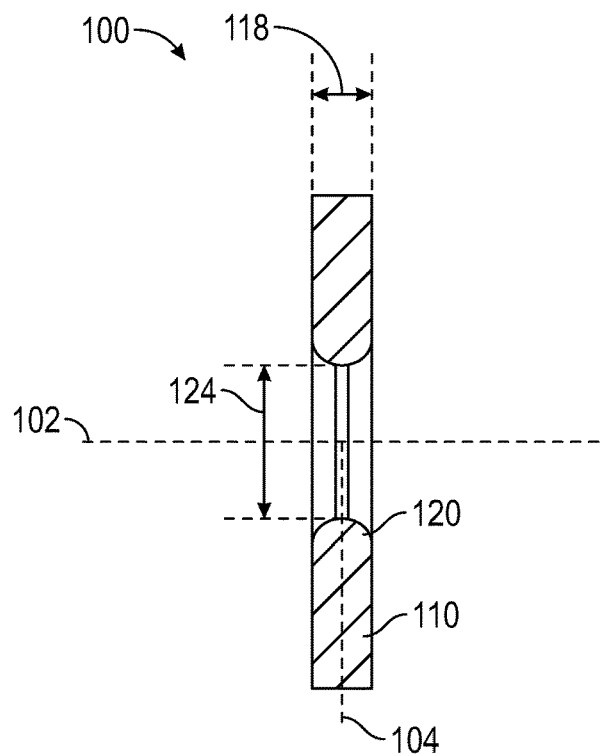
FIG. 3 is a cross section of the device of FIG. 2, taken along the line 3-3.

FIG. 3 is cross section of the device of FIG. 2, taken along the line 3-3. As shown, the central axis extends through the central aperture 122 perpendicular to the radial direction 104.

The annular disc portion 110 of the device 100 can have first surface 117 opposite a second surface 119, defining a disc thickness 118. The disc thickness 118 can vary based on the composition of the device 100 and the desired total weight or mass. The disc thickness 118 can be one inch or less. However, the disc thickness 118 can also be larger than one inch. In some embodiments, the disc thickness 118 can be 0.25 inches, or 0.5 inches, depending on the desired weight of the device 100. In general, the lower weight denominations may have a narrower disc thickness 118. The first surface 117 and the second surface 119 can each be flat surfaces.

Figure 4:
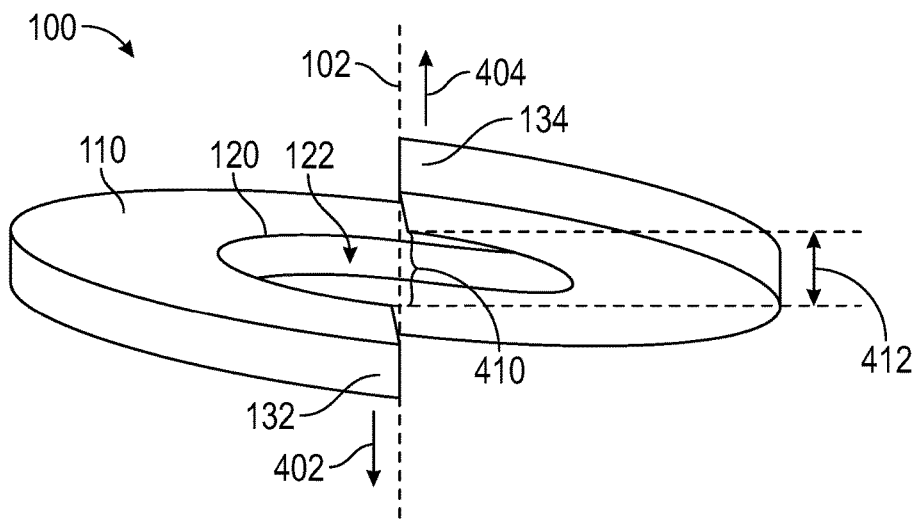
FIG. 4 is another perspective view of the device of FIG. 1.

FIG. 4 another perspective view of the device of FIG. 1. In some embodiments, the device 100 can be manipulated (e.g., twisted) in an axial direction (e.g., along the central axis 102) drawing the first end 132 away from the second end 134. This can draw the first end in a first direction 402 and the second end in a second direction 404 to create a gap 410. The gap 410 can have a gap width 412. When the first end 132 and the second end 134 are drawn in opposite directions (e.g., the first direction 402 and the second direction 404), the gap width 412 can be similar to (e.g., slightly larger than) that of a width of a bar or handle of the host apparatus (see, e.g., FIG. 5, FIG. 12, FIG. 13).

In some embodiments, the device 100 can be formed such that is substantially flat (e.g., in the radial direction) when at rest. The device 100 can also have a structural memory or elasticity that returns the device 100 to its original, flat shape after manipulation. For example, when a twisting force is applied to the first end 132 and the second end 134, the radial slot 130 allows the gap 410 to expand to the gap width 412 to fit over the bar (FIG. 5) or handle of the host apparatus to which the device 100 is being attached. Once in place over the bar or handle of the host apparatus, the twisting force is released from the first end 132 and the second end 134, and the device 100 can return to its flat rest state. In some embodiments, the application of the device 100 to the host apparatus in this manner causes the ring portion 120 to squeeze around the bar or handle of the host apparatus with sufficient force to maintain its position throughout use in, for example, a fitness or weightlifting routine.

The material or materials used to form or manufacture the disc portion 110 and the ring portion 120 can be sufficiently flexible to allow the radial slot 130 and the gap 410 to achieve sufficient expansion when from the application of easily-achievable twisting forces produced by a human user. The materials (e.g., the device 100) may also have sufficient shape-memory to enable the deflected device 100 to elastically return into a flat, at-rest position. This shape-memory can provide the required coupling to the host apparatus.

FIG. 5 is a perspective view of the device of FIG. 1 installed on a host apparatus. A host apparatus 500 can be a barbell or a dumbbell, for example. The host apparatus 500 can have a bar 502 and a plurality of plates 504. In some examples, the may be even numbers of the plate 504, that is, distributed on either end of the bar 502 for balance. In some other examples, there may be an uneven number of plates 504 on the host apparatus 500.

The bar 502 can have a bar diameter 510. The bar diameter 510 can be similar to the inner diameter 124 of the central aperture 122. In some embodiments, the bar diameter 510 can be smaller than the inner diameter 124.

The plate 504 can have a plate outer diameter 506. The disc outer diameter 114 (FIG. 1) can be similar to a plate outer diameter 506. In some examples, the plate 504 can have the same disc outer 114 diameter of the disc portion 110. However, generally the disc outer diameter 114 can be smaller than the plater outer diameter 506. In some embodiments, the disc outer diameter 114 can be five inches or less. The outer diameter 506 of the plate 504 can vary based on the weight of the host apparatus 500 and the disc outer diameter 114 should remain smaller than the outer diameter 506 to prevent interference with the use of the host apparatus 500. Thus the disc outer diameter 114 of the device 100 can be 3, 4, or 5 inches, or any partial measurement therebetween. In some embodiments the disc outer diameter 114 can be larger than 5 inches for use with larger host apparatuses 500. The disc outer diameter 114 can further depend on the total weight of the device 100.

In some embodiments more than one device 100 can be applied to the host apparatus 500. Two devices 100 are shown here as device 100a and device 100b. For example, a fixed-weight barbell or dumbbell (e.g., similar to the host apparatus 500) may not have a flexible weight configurations for the user. Accordingly, one or more pairs of the device 100 can be applied to the bar 502 to increase the total weight or mass of the host apparatus 500 by a desired, incremental amount. The device 100 can be used in pairs on the host apparatus 500 to maintain symmetry and even weight distribution during exercises. However, in some other embodiments (see FIG. 12) only a single device 100 or an uneven number of devices 102 can be applied to the host apparatus 500.

Figure 6:
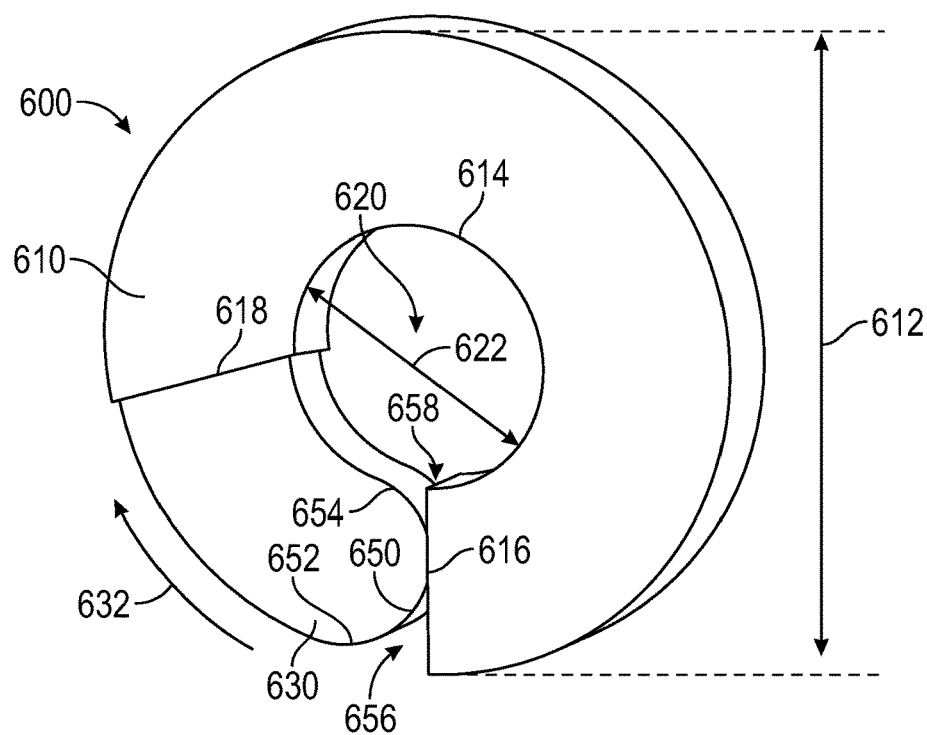
FIG. 6 is a perspective view of another embodiment of the device of FIG. 1.

FIG. 6 is a perspective view of another embodiment of the device of FIG. 1. A fine weight adjustment device (device) 600 can be similar to the device 100 and adapted to fit onto the bar 502 of the host apparatus 500 or other weight-lifting apparatus, for example. The device 600 can have a disc body 610. The disc body 610 can have an arcuate shape, forming a portion of an annulus. The device 600 can also have a retractable arm 630 that can complete a disc or annular structure of the device 600. The device 600 can have an outer diameter 612 similar to the disc outer diameter 114 (FIG. 1). The disc body 610 and the retractable arm 630 can further have a disc inner perimeter 614 defining a disc central aperture 620. The disc central aperture 620 can have an inner disc diameter 622 that is sized to receive the bar 502, for example.

The disc body 610 can have a disc first end 616 and a disc second end 618. The disc second end 618 can have an opening that extends inside the disc body 610 forming a hollow interior 611 (FIG. 7) that can surround the retractable arm 630 in a clearance fit. The retractable arm 630 can be housed within the hollow interior 611 of the disc body 610 proximate the disc second end 618. The retractable arm 630 can move, or retract, in a direction 632 within the hollow interior 611. As the retractable arm 630 moves into the hollow interior 611 of the disc body 610 from the disc second end 618, it can compress an internal spring mechanism 634 (FIG. 7) within the disc body 610.

In some embodiments, the retractable arm 630 can have a rounded end 650. The rounded end 650 can have a round exterior portion 652 and a rounded interior portion 654. In some embodiments, the rounded end 650 can contact a disc first end 616. The internal spring mechanism 634 can provided an amount of radial force that can maintain contact between the rounded end 650 and the disc first end 616. Accordingly, the rounded exterior portion 654 can define an outer opening 656 and the rounded interior portion 654 can form an inner opening 658. The outer opening 656 can be sized and formed to receive the bar 502. The rounded exterior portion 652 can have a curvature that can force the retractable arm 630 to retract within the disc body 610 when the bar 502 is pushed into the outer opening 656. Accordingly, the curvature of the rounded exterior portion 652 may have a different curvature than that shown in FIG. 6 and FIG. 7. The curvature of the rounded exterior portion 652 and the rounded interior portion 654 can have other curvatures (e.g., asymmetrical, concave, convex, etc.) to allow the bar 502 to force the retractable arm 630 to move in the direction 632. In some embodiments, the device 600 can be snapped into place around the bar 502 by pressing the bar 502 into the outer opening 656. In some other embodiments, the retractable arm 630 can be manually moved to position the device 600 around the bar 502.

Figure 7:
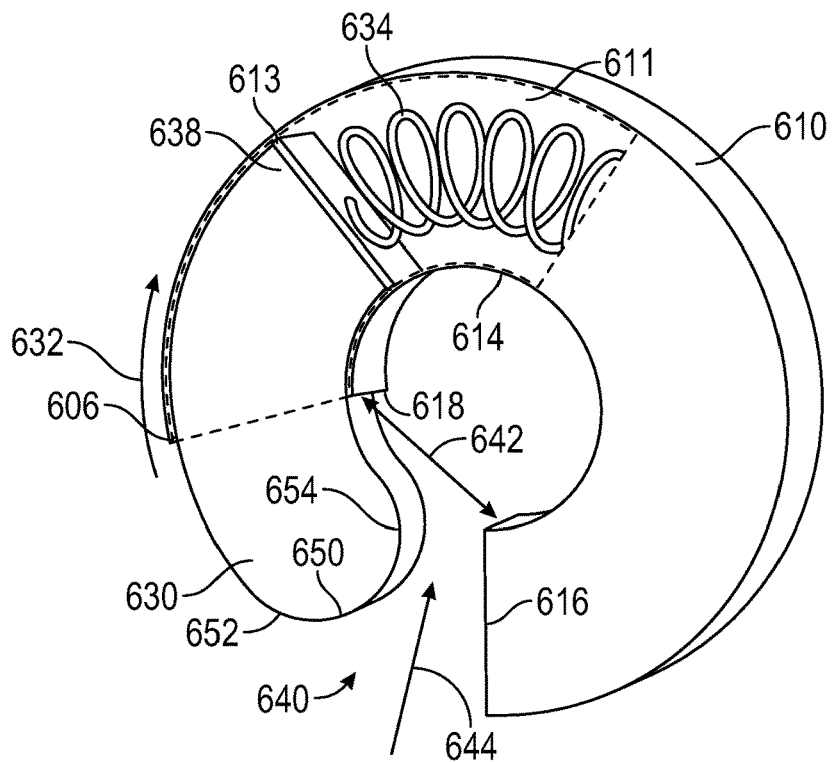
FIG. 7 is perspective cutaway view of the device of FIG. 6.

FIG. 7 is a cutaway view of the device of FIG. 6. The spring mechanism 634 can have a spring first end 635 in contact with the interior end 638. The internal spring mechanism 634 can also have a spring second end (not shown) coupled to or within contact with a portion of the disc body 610 on the hollow interior 611. The internal spring mechanism 634 can provide a force to the retractable arm 630 to maintain a closed resting position. A force can be applied to the retractable arm 634, that can compress the internal spring mechanism and move the retractable arm 634 within the hollow interior 611. As the retractable arm 630 is retracted within disc body 610, the internal spring mechanism 634 is compressed, providing a disc opening 640. The disc opening 640 opens to a gap width 642 that is sufficient to receive the bar 502 (FIG. 5), for example. Accordingly, the gap width 642 can be slightly larger than the bar diameter 510. The gap width 642 can also be similar to the inner disc diameter 622.

As the bar 502 is moved in a direction 644 into the disc central aperture 620, the retractable arm 630 can move in a direction opposite of the direction 632 and return to its original position as the internal spring mechanism 634 extends, moving the retractable arm 630 toward the closed position as shown in FIG. 6. The device 600 is then secured in place, surrounding the bar 502. The internal spring mechanism 634 is shown as a conventional circular spring; however the skilled person will appreciate that the internal spring mechanism can be another kind of spring mechanism to provide a force. In some embodiments, the internal spring mechanism 634 can be another kind of wire or metallic spring or a compressible fluid (e.g. air, gas, hydraulic) cylinder, for example.

In some embodiments, the retractable arm 630 can have a retainer lip 636. The retainer lip 636 can be formed around an interior end 638 of the retractable arm 630. The retainer lip 636 can provide an another degree of security for the retractable arm 630 as it can come in contact with a securing lip 606 formed in the second end 618 of the disc body 610. In some embodiments, the securing lip 606 can come in contact with the retainer lip 636 of the retractable arm 630 when the interior spring mechanism 634 is extended and the rounded end 650 is in contact with the disc first end 616. This can prevent the retractable arm 630 from departing the disc body 610 under the force of the internal spring mechanism 634.

In some embodiments, the rounded interior portion 654 can function similarly to the rounded exterior portion 652. If the device 600 needs to be removed from the bar 502, the inner opening 658 and the rounded interior portion 654 can provide sufficient room to pull the device 600 clear of the bar 502. The retractable arm 630 can be retracted within the disc body 610 similar to above and the device 600 can be removed. This can be accomplished by manually drawing the disc body 610 away from the bar 502 or manually compressing the retractable arm 630 to provide the disc opening 640.

Figure 8A:
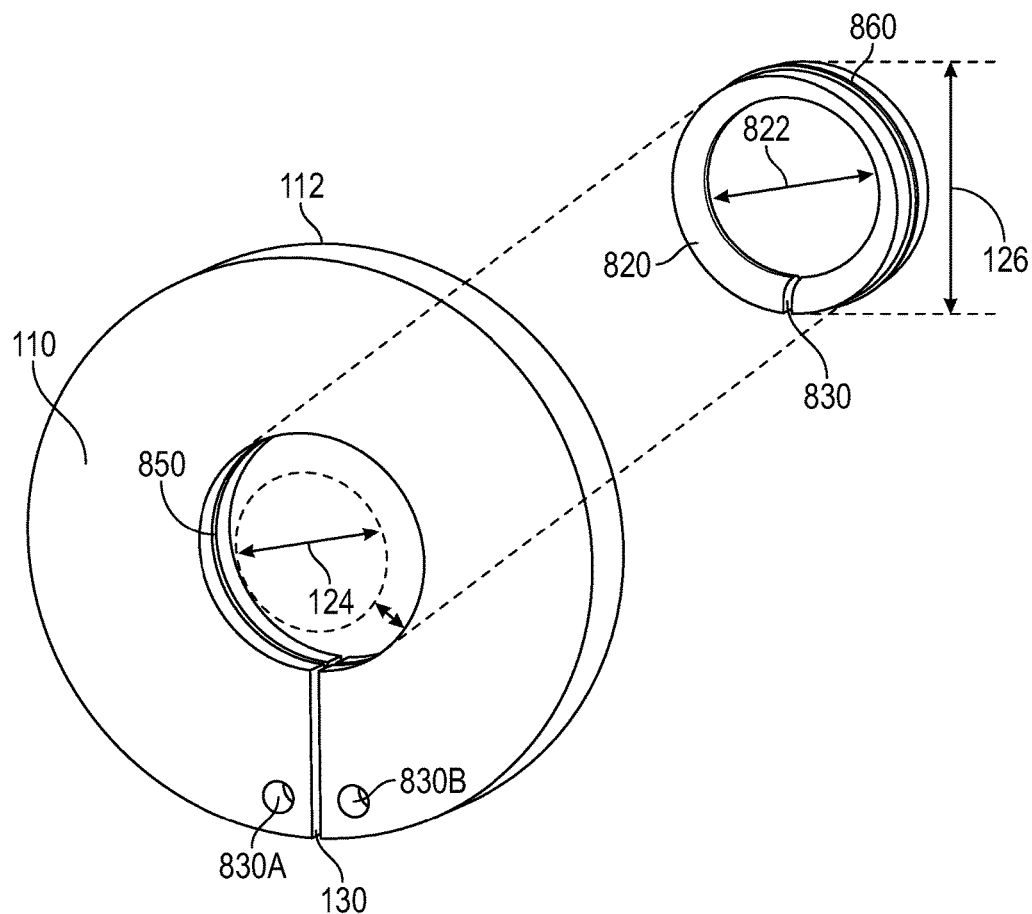
FIG. 8A is an exploded view of an embodiment of the device of FIG. 1.

FIG. 8A is an exploded view of an embodiment of the device of FIG. 1. In some embodiments, the ring portion 120 can be detachable from the disc portion 110. Detaching the ring portion 120 can leave the disc portion 110 as shown. In such an embodiment, a ring portion 820 can be provided. The inner ring 820 can be an adapter, allowing the device 100 to be used with different host apparatuses 500 having varying bar diameters 510.

The ring portion 820 can have an outer ring diameter 126 (FIG. 2), the same as the ring portion 120, providing a one-for-one exchange of parts. This can allow the ring portion 820 to easily fit within the disc portion 110. The inner ring 820 can have an inner ring diameter 822. The inner ring diameter 822 can be different than the inner ring diameter 124 (FIG. 1). This can provide the ability to adapt the use of the device 100 to, for example, a different bar diameter 510. In some embodiments, the inner ring diameter 822 is smaller than the inner ring diameter 124. In some other embodiments, it can be bigger, providing flexibility to use the device 100 with other host apparatuses 500. The inner ring 820 can further have a slot 830 that coincides with the slot 130, in use. The desired weight of the inner ring 820 can be adapted to compensate for increase or decrease in size, as compared to the ring portion 120. Accordingly, the same weight/mass of the device 100 can be maintained regardless of which inner ring 820 is used.

In some embodiments, the device 100 can also have securing holes 830. The securing holes 830 are depicted individually as securing holes 830a, 830b, but may be referred to collectively as securing holes 830. The securing holes 830 can provide a means for securing the device 100 to the host apparatus 500. In some embodiments, a piece of line, rope, elastic, or bungee can be weaved or tied through the securing holes to prevent the device 100 from inadvertently disengaging from the host apparatus 500. Though not specifically shown, the securing holes 830 can also be adapted for use on the device 600 with the retractable arm 630. For example, a securing hole 830*a* can be formed in the rounded end 650, while the securing hole 830*b* can be formed in the first end 616.

Figure 8B:
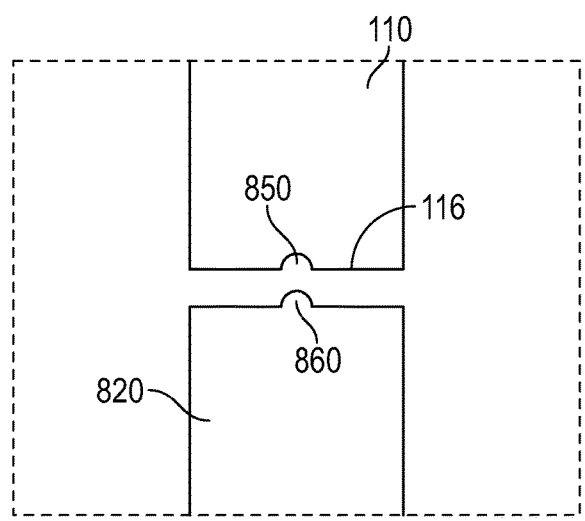
FIG. 8B is a detailed view of a portion of the inner ring and a portion of the disc portion of FIG. 8, near their interference fit along the disc inner perimeter.

FIG. 8B is a detailed view of a portion of the inner ring and a portion of the disc portion of FIG. 8, near their interference fit along the disc inner perimeter. In some embodiments, the disc inner perimeter 116 (FIG. 1) of the disc portion 110 can have an annular groove 850. The annular groove 850 is also shown in FIG. 8A, for reference. Additionally, the inner ring 820 can have a perimetric nub 860, formed to fit within the annular groove 850. In some embodiments, the inner ring 120 (FIG. 1) can also be formed with the perimetric nub 860. This can allow a one-for-one swap of the inner ring 120 for the inner ring 820 if a different inner ring diameter 822 is needed for a specific bar diameter 510. When the inner ring 820 (or e.g., the inner ring 120) is fit within the disc portion 110, the annual groove 850 can receive the perimetric nub 860 to maintain the relative position between the two components.

FIG. 9 is a perspective view of another embodiment of the device of FIG. 1. In some embodiments, the device 100 can have certain internal electronics. For example, the device 100 can have a fitness monitor 900. The fitness monitor 900 can track at least one of acceleration, force, and time. In some other embodiments, a three-dimensional measurement of movement (e.g., acceleration or velocity in x, y, z, axes) or a determination of work (e.g., work=force*distance) performed by the user can be measured or calculated. The fitness monitor 900 can be permanently affixed within the device 100. In some embodiments, the fitness monitor 900 can be removable and/or rechargeable. The ability to remove the fitness monitor 900 from the device 100 can facilitate charging and/or downloading data. The fitness monitor 900 can also be adapted to communicate with a mobile wireless device 920, such as a smartphone or other tracking device. During a fitness or weightlifting routine, the host apparatus 500 can be moved around forcefully. Accordingly, the acceleration of the device 100 (and the host apparatus 500) or the force applied thereto can be a useful measure of intensity of the workout or fitness levels.

FIG. 10 is a functional block diagram of the fitness monitor of FIG. 9. The fitness monitor 900 can have an accelerometer 910. The accelerometer 910 can track acceleration and/or position and orientation of the device 100 and hence the host apparatus 500. The fitness monitor 900 can also have a controller 902 operably coupled to the accelerometer 910. The controller 902 can be one or more processors or microprocessors that control the functions of the fitness monitor 900. The controller 902 can store information from the accelerometer 910 to a memory 904 operably coupled to the controller 902. The memory 904 can store fitness information for later download or transmission to the mobile wireless device 920. The memory 904 can further store software, various computer programs or code, or other instructions, accessible by the controller, to carry out the functions of the fitness monitor 900.

The fitness monitor 900 can also have a battery 906 coupled to the controller 902 to store and provide power. The fitness monitor 900 can also have a transceiver 908 coupled to the controller 902. The transceiver 908 can wirelessly transmit live or stored fitness information stored to the memory 904. The transceiver 908 can receive input from, for example, the user, regarding a weight of the host apparatus 500 that the controller 902 can store to the memory 904. The controller 902 can use such information to calculate or determine fitness levels, force applied to the host apparatus 500, and similar metrics. Such information can be input or received via the wireless device 920.

The fitness monitor 900 can also have an input/output port (port) 912 operably coupled to at least one of the controller 902, the memory 904, the battery 906, and the transceiver 908. The port 912 can provide a means for recharging the battery 906 or transferring the fitness information from the memory 904. In some embodiments, the port 912 can be a wireless charging port allowing the battery 906 to be recharged without removing the fitness monitor 900 from the device 100.

FIG. 11 is a perspective view of another embodiment of the device of FIG. 9. In some embodiments, the device 100 can have an inner ring 950. The inner ring 950 can be similar to the removable inner ring 820. The inner ring 950 can have an embodiment of the fitness monitor 900 embedded within it. This can allow a retrofit of the device 100 having the inner ring 120 (FIG. 1) to be used with the fitness monitor 900 (FIG. 10). In some embodiments, the inner ring 950 can have an inner radius 952, defining an aperture 954 to receive the bar 502, for example, similar to the embodiments described above.

Figure 12:
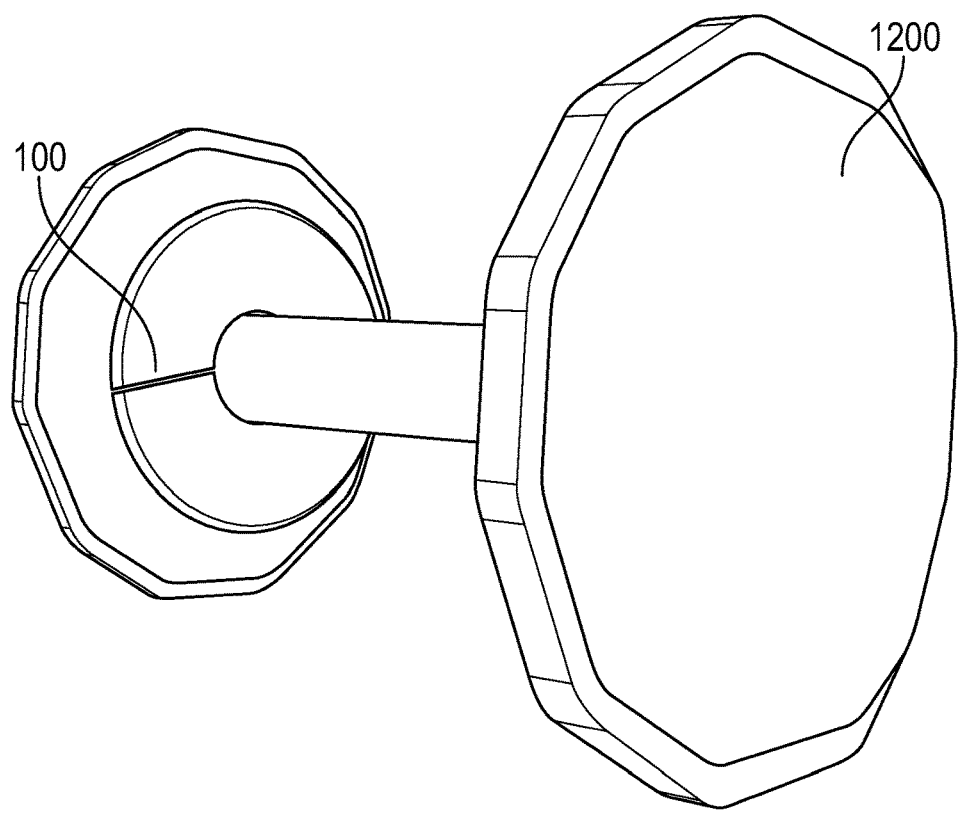
FIG. 12 is a perspective view of an embodiment of the device of FIG. 1 installed on a barbell.

FIG. 12 is a perspective view of an embodiment of the device of FIG. 1 installed on a barbell. In some embodiments, as disclosed herein, the device 100 can be installed on various host devices 500. As shown, the device 100, (or any associated embodiments disclosed herein) can be installed on a dumbbell 1200. The dumbbell 1200 can have a fixed-weight or mass. The device 600 can also be installed on the dumbbell 1200 as needed. The disc outer diameter 114 (FIG. 1) of the device 100 shown can be smaller than an out diameter 1202 of the dumbbell 1200. One or more of the devices 100 can be added to increase the overall weight/mass of the dumbbell 1200 by a desired increment.

Figure 13:
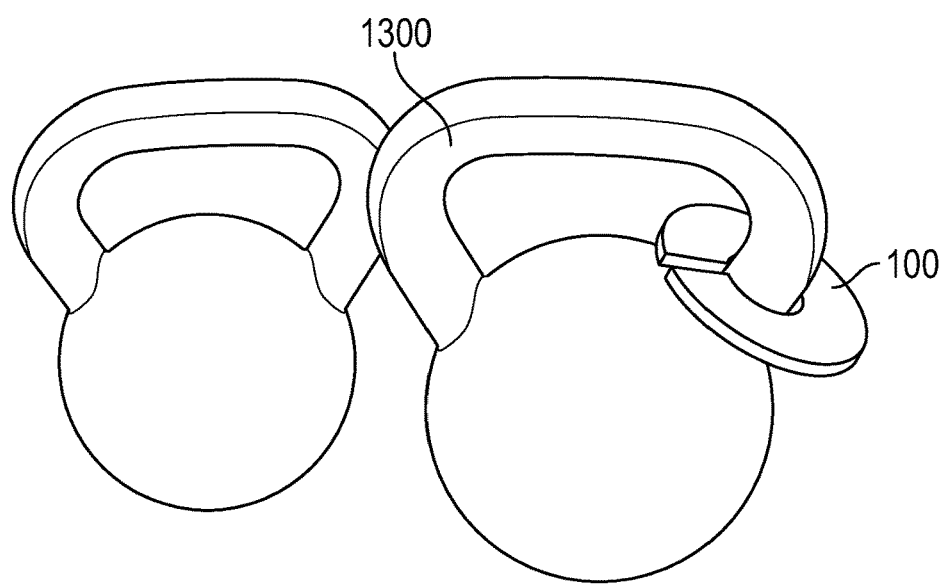
FIG. 13 is a perspective view of an embodiment of the device if FIG. 1 installed on a kettle bell.

FIG. 13 is a perspective view of an embodiment of the device if FIG. 1 installed on a kettle bell. In some embodiments, the device 100 can be installed on another host apparatus 500 such as a kettle bell 1300. The kettle bell 1300 generally has a fixed weight. The kettle bell 1300 can come in fixed increments of 5 or 10 kg or lbs. Accordingly, the device 100 can be installed or affixed to the kettle bell 1300 to increase the overall weight/mass of the kettle bell 1300 in an incremental or progressive manner as desired.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A device for fine weight adjustment of a host apparatus having a bar with a bar diameter, the device comprising:
   an annular body comprising
      an outer disc perimeter defining a disc plane,
      an inner disc perimeter, wherein the inner disc perimeter defines a central aperture, and wherein the central aperture comprises a diameter compatible with the bar diameter of the host apparatus,
      a disc portion, and
      a ring portion,
         wherein the disc portion comprises the inner disc perimeter sized to receive the ring portion;
   a central axis extending in an axial direction through a center of the annular body and disposed orthogonal to the disc plane, wherein said axial direction comprises a direction along said central axis; and,
a slot extending in a radial direction through the annular body from the outer disc perimeter to said inner disc perimeter and defining a first disc end and a second disc end separated by a slot width,
wherein said radial direction comprises a direction away from said central axis;
wherein the annular body is deformable and twistable from said radial direction to said axial direction to allow the first disc end to be deflected away from the second disc end in a direction
away from and orthogonal to the disc plane, and along the central axis,
such that said slot becomes an axial gap in the axial direction with an axial gap width in the axial direction, and such that when a twisting force is applied to said annular body to twist said annular body from said radial direction to said axial direction to deflect said first disc end in said direction away from and orthogonal to the disc plane and along the central axis
said first disc end is deflected away from said second disc end, and
said first disc end is drawn in a first direction and said second disc end is drawn in a second direction, wherein said first direction and said second direction are opposite directions,
such that when said first disc end and said second disc end are drawn in said opposite directions, said axial gap in said axial direction is opened and said axial gap width expands in said axial direction to a width larger than that of a width of said bar of said host apparatus with sufficient width to receive said bar in said slot in said axial direction, and
wherein the annular body is formed of a material comprising an elasticity sufficient to allow axial flexibility that returns the annular body to its original shape in said radial direction after being deformed and twisted in said axial direction.

2. The device of claim 1 wherein when the first disc end and the second disc end are twisted in opposite directions along the central axis, the central aperture is capable of receiving the bar of the host apparatus.

3. The device of claim 1 wherein the disc portion further comprises an annular groove formed about the disc inner perimeter and the ring portion comprises a perimetric nub formed about an outer ring perimeter formed to fit within the annular groove.

4. The device of claim 1 wherein the slot width is between 0.05 inches to 0.2 inches.

5. The device of claim 1 wherein the first disc end and the second disc end comprise a magnetic material such that the first end and the second end are magnetically attracted to each other.

6. The device of claim 1 further comprising a fitness monitor operable to measure acceleration of the device.

7. The device of claim 1 further comprising a securing hole formed in each of the first end and the second end.

8. The device of claim 1 further comprising a total weight of one-half pound, one pound, two pounds, one kilogram, three pounds, four pounds or five pounds.

9. The device of claim 1 further comprising a total weight between one-quarter pound and one pound inclusive.

10. A device for fine weight adjustment of a host apparatus for use in fitness activities, the host apparatus having a bar with a bar diameter, the device comprising:
an annular body comprising a disc portion that comprises
an outer disc perimeter defining a disc plane, and
an inner disc perimeter, wherein the inner disc perimeter defines a central aperture, and wherein the central aperture comprises a diameter sufficient to receive the bar diameter of the host apparatus;
a central axis extending in an axial direction through a center of the annular body and disposed orthogonal to the disc plane,
wherein said axial direction comprises a direction along said central axis;
a slot extending in a radial direction through the annular body from the outer disc perimeter to said inner disc perimeter and defining a first disc end and a second disc end separated by a slot width,
wherein said radial direction comprises a direction away from said central axis; and,
a weight element disposed within the annular body;
wherein the annular body is deformable and twistable from said radial direction to said axial direction to allow the first disc end to be deflected away from the second disc end in a direction
away from and orthogonal to the disc plane and along the central axis,
such that said slot becomes an axial gap in the axial direction with an axial gap width in the axial direction, and such that when a twisting force is applied to said annular body to twist said annular body from said radial direction to said axial direction to deflect said first disc end in said direction away from and orthogonal to the disc plane and along the central axis
said first disc end is deflected away from said second disc end, and
said first disc end is drawn in a first direction and said second disc end is drawn in a second direction, wherein said first direction and said second direction are opposite directions,
such that when said first disc end and said second disc end are drawn in said opposite directions, said axial gap in said axial direction is opened and said axial gap width expands in said axial direction to a width larger than that of a width of said bar of said host apparatus with sufficient width to receive said bar in said slot in said axial direction.

11. The device of claim 1 wherein the disc portion is formed with an annular groove, and wherein the annular body further comprises
a ring portion having an outer ring diameter sized to fit within the disc inner perimeter and a perimetric nub formed about an outer ring perimeter formed to fit within the annular groove.

12. A device for fine weight adjustment of a host apparatus having a bar with a bar diameter, the device comprising:
an annular body comprising
an outer disc perimeter defining a disc plane, and
an inner disc perimeter, wherein the inner disc perimeter defines a central aperture, and wherein the central aperture comprises a diameter compatible with the bar diameter of the host apparatus;

a central axis extending in an axial direction through a center of the annular body and disposed orthogonal to the disc plane,
wherein said axial direction comprises a direction along said central axis; and,
a slot extending in a radial direction through the annular body from the outer disc perimeter to said inner disc perimeter and defining a first disc end and a second disc end separated by a slot width,
wherein said radial direction comprises a direction away from said central axis, and
wherein said first disc end and said second disc end comprise a magnetic material such that said first disc end and said second disc end are magnetically attracted to each other;
wherein the annular body is deformable and twistable from said radial direction to said axial direction to allow the first disc end to be deflected away from the second disc end in a direction
away from and orthogonal to the disc plane, and
along the central axis,
such that said slot becomes an axial gap in the axial direction with an axial gap width in the axial direction, and such that when a twisting force is applied to said annular body to twist said annular body from said radial direction to said axial direction to deflect said first disc end in said direction away from and orthogonal to the disc plane and along the central axis
said first disc end is deflected away from said second disc end, and
said first disc end is drawn in a first direction and said second disc end is drawn in a second direction, wherein said first direction and said second direction are opposite directions,
such that when said first disc end and said second disc end are drawn in said opposite directions, said axial gap in said axial direction is opened and said axial gap width expands in said axial direction to a width larger than that of a width of said bar of said host apparatus with sufficient width to receive said bar in said slot in said axial direction, and
wherein the annular body is formed of a material comprising an elasticity sufficient to allow axial flexibility that returns the annular body to its original shape in said radial direction after being deformed and twisted in said axial direction.

13. A device for fine weight adjustment of a host apparatus having a bar with a bar diameter, the device comprising:
an annular body comprising
an outer disc perimeter defining a disc plane, and
an inner disc perimeter, wherein the inner disc perimeter defines a central aperture, and wherein the central aperture comprises a diameter compatible with the bar diameter of the host apparatus;
a central axis extending in an axial direction through a center of the annular body and disposed orthogonal to the disc plane,
wherein said axial direction comprises a direction along said central axis;
a slot extending in a radial direction through the annular body from the outer disc perimeter to said inner disc perimeter and defining a first disc end and a second disc end separated by a slot width,
wherein said radial direction comprises a direction away from said central axis; and,
a total weight of one-half pound or one pound or two pounds or one kilogram or three pounds or four pounds or five pounds;
wherein the annular body is deformable and twistable from said radial direction to said axial direction to allow the first disc end to be deflected away from the second disc end in a direction
away from and orthogonal to the disc plane, and
along the central axis,
such that said slot becomes an axial gap in the axial direction with an axial gap width in the axial direction, and such that when a twisting force is applied to said annular body to twist said annular body from said radial direction to said axial direction to deflect said first disc end in said direction away from and orthogonal to the disc plane and along the central axis
said first disc end is deflected away from said second disc end, and
said first disc end is drawn in a first direction and said second disc end is drawn in a second direction, wherein said first direction and said second direction are opposite directions,
such that when said first disc end and said second disc end are drawn in said opposite directions, said axial gap in said axial direction is opened and said axial gap width expands in said axial direction to a width larger than that of a width of said bar of said host apparatus with sufficient width to receive said bar in said slot in said axial direction, and
wherein the annular body is formed of a material comprising an elasticity sufficient to allow axial flexibility that returns the annular body to its original shape in said radial direction after being deformed and twisted in said axial direction.

14. A device for fine weight adjustment of a host apparatus having a bar with a bar diameter, the device comprising:
an annular body comprising
an outer disc perimeter defining a disc plane, and
an inner disc perimeter, wherein the inner disc perimeter defines a central aperture, and wherein the central aperture comprises a diameter compatible with the bar diameter of the host apparatus;
a central axis extending in an axial direction through a center of the annular body and disposed orthogonal to the disc plane,
wherein said axial direction comprises a direction along said central axis;
a slot extending in a radial direction through the annular body from the outer disc perimeter to said inner disc perimeter and defining a first disc end and a second disc end separated by a slot width,
wherein said radial direction comprises a direction away from said central axis; and,
a total weight between one-quarter pound and one pound inclusive;
wherein the annular body is deformable and twistable from said radial direction to said axial direction to allow the first disc end to be deflected away from the second disc end in a direction
away from and orthogonal to the disc plane, and
along the central axis, such that said slot becomes an axial gap in the axial direction with an axial gap width in the axial direction, and such that when a twisting force is applied to said annular body to twist said annular body from said radial direction to said axial direction to deflect said first disc end in said direction away from and orthogonal to the disc plane and along the central axis said first disc end is deflected away from said second disc end, and said first disc end is drawn in a first direction and said second disc end is drawn in a second direction, wherein said first direction and said second direction are opposite directions, such that when said first disc end and said second disc end are drawn in said opposite directions, said axial gap in said axial direction is opened and said axial gap width expands in said axial direction to a width larger than that of a width of said bar of said host apparatus with sufficient width to receive said bar in said slot in said axial direction, and wherein the annular body is formed of a material comprising an elasticity sufficient to allow axial flexibility that returns the annular body to its original shape in said radial direction after being deformed and twisted in said axial direction.

\* \* \* \* \*